US008359912B2

(12) United States Patent (10) Patent No.: US 8,359,912 B2
Schneider et al. (45) Date of Patent: Jan. 29, 2013

(54) AUTOMATIC ENGINE OIL LIFE DETERMINATION ADJUSTED FOR CONSUMED VOLUME OF OIL

(75) Inventors: Eric W. Schneider, Shelby Township, MI (US); Matthew J. Snider, Howell, MI (US); David R. Staley, Flushing, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 358 days.

(21) Appl. No.: 12/857,634

(22) Filed: Aug. 17, 2010

(65) Prior Publication Data

US 2012/0042718 A1 Feb. 23, 2012

(51) Int. Cl.
*G01M 15/00* (2006.01)
(52) U.S. Cl. .................................................. 73/114.55
(58) Field of Classification Search ................. 73/53.05, 73/114.55, 114.56
See application file for complete search history.

(56) References Cited

U.S. PATENT DOCUMENTS

| | | | | |
|---|---|---|---|---|
| 4,706,193 A * | 11/1987 | Imajo et al. | ................... | 701/29.5 |
| 5,273,134 A * | 12/1993 | Hegemier et al. | .............. | 184/6.4 |
| 7,614,284 B2 * | 11/2009 | Snider et al. | .................. | 73/53.05 |
| 7,793,537 B2 * | 9/2010 | Benz et al. | ................... | 73/114.55 |
| 7,908,912 B2 * | 3/2011 | Van Weelden et al. | ..... | 73/114.56 |
| 7,946,159 B2 * | 5/2011 | Despres et al. | ............. | 73/114.56 |
| 8,103,462 B2 * | 1/2012 | Liu et al. | .......................... | 702/55 |
| 8,179,242 B2 * | 5/2012 | Schneider | ...................... | 340/438 |
| 8,234,915 B2 * | 8/2012 | Schneider et al. | ......... | 73/114.55 |
| 2004/0093150 A1 * | 5/2004 | Arai et al. | ...................... | 701/104 |
| 2009/0120176 A1 * | 5/2009 | Despres et al. | ............ | 73/114.52 |
| 2010/0250156 A1 * | 9/2010 | Halalay et al. | .................. | 702/50 |
| 2010/0300188 A1 * | 12/2010 | Halalay et al. | ............. | 73/114.55 |
| 2012/0042717 A1 * | 2/2012 | Schneider et al. | ......... | 73/114.55 |
| 2012/0042719 A1 * | 2/2012 | Schneider et al. | ......... | 73/114.55 |
| 2012/0044065 A1 * | 2/2012 | Schneider et al. | ......... | 340/457.4 |
| 2012/0044077 A1 * | 2/2012 | Blossfeld et al. | ............. | 340/603 |
| 2012/0046920 A1 * | 2/2012 | Blossfeld et al. | ................. | 703/2 |
| 2012/0209460 A1 * | 8/2012 | Jacques et al. | .................. | 701/22 |

* cited by examiner

Primary Examiner — Eric S McCall
(74) Attorney, Agent, or Firm — Quinn Law Group, PLLC

(57) ABSTRACT

A method is provided for determining remaining oil life prior to an oil change in an internal combustion engine that uses a body of oil. The method includes transferring the body of oil to the engine and determining a volume of the transferred body of oil. The method also includes determining a volume of oil consumed by the engine from the transferred body of oil and determining the remaining oil life based on the determined volume of the body of oil and the determined volume of oil consumed. The method additionally includes activating an oil change indicator when the remaining oil life reaches a predetermined level. A system for determining a number of engine revolutions permitted on a volume of oil is also disclosed.

20 Claims, 2 Drawing Sheets

AUTOMATIC ENGINE OIL LIFE DETERMINATION ADJUSTED FOR CONSUMED VOLUME OF OIL

TECHNICAL FIELD

The present invention relates to a system for automatic engine oil life determination adjusted for a volume of oil consumed by the engine.

BACKGROUND

In internal combustion engines, oil is typically used for lubrication, cleaning, inhibiting corrosion, to improve sealing, and to cool the engine by carrying heat away from the moving parts. Engine oils are generally derived from petroleum-based and non-petroleum synthesized chemical compounds. Modern engine oils are mainly blended by using base oil composed of hydrocarbons and other chemical additives for a variety of specific applications. Over the course of oil's service life, engine oil frequently becomes contaminated with foreign particles and soluble contaminants, and its chemical properties become degraded due to oxidation and nitration. A common effect of such contamination and degradation is that the oil may lose its capability to fully protect the engine, thus necessitating the used oil to be changed or replaced with clean, new oil.

Engine oil is generally changed based on time in service, or based on a distance the engine's host vehicle has traveled. Actual operating conditions of the vehicle and hours of engine operation are some of the more commonly used factors in deciding when to change the engine oil. Time-based intervals account for shorter trips where fewer miles are driven, while building up more contaminants. During such shorter trips, the oil may often not achieve full operating temperature long enough to burn off condensation, excess fuel, and other contamination that may lead to "sludge", "varnish", or other harmful deposits.

To aid with timely oil changes, modern engines often include oil life monitoring systems to estimate the oil's condition based on factors which typically cause degradation, such as engine speed and oil or coolant temperature. When an engine employing an oil life monitoring system is used in a vehicle, such a vehicle's total distance traveled since the last oil change may be an additional factor in deciding on the appropriate time for an oil change.

SUMMARY

A method is disclosed herein for determining remaining oil life prior to an oil change in an internal combustion engine that uses a body of oil. The method includes transferring the body of oil to the engine and determining a volume of the transferred body of oil. The method also includes determining a volume of oil consumed by the engine from the transferred body of oil and determining the remaining oil life based on the determined volume of the body of oil and the determined volume of oil consumed. The method additionally includes activating an oil change indicator when the remaining oil life reaches a predetermined level.

The method may additionally include resetting the oil change indicator to represent 100% of oil life remaining following the oil change. At least one of the acts of determining a volume of the transferred body of oil, determining a volume of oil consumed by the engine, determining the remaining oil life, and activating and resetting the oil change indicator may be accomplished via a controller arranged relative to and operatively connected to the engine.

The engine may include an oil sump arranged to accept the transferred body of oil. The act of determining a volume of the transferred body of oil may include determining a level of the transferred body of oil in the sump. The act of determining the remaining oil life may further include determining a number of revolutions for each combustion event of the engine and determining a number of combustion events permitted using the determined volume of oil.

The act of determining a volume of oil may be accomplished via a device configured to provide a signal indicative of the volume of oil consumed by the engine. The act of determining a volume of oil consumed by the engine may be accomplished based on a predetermined rate of oil consumption.

A system for determining the remaining oil life permitted on a volume of oil is also disclosed.

The above features and advantages and other features and advantages of the present invention are readily apparent from the following detailed description of the best modes for carrying out the invention when taken in connection with the accompanying drawings.

DETAILED DESCRIPTION

Figure 1:
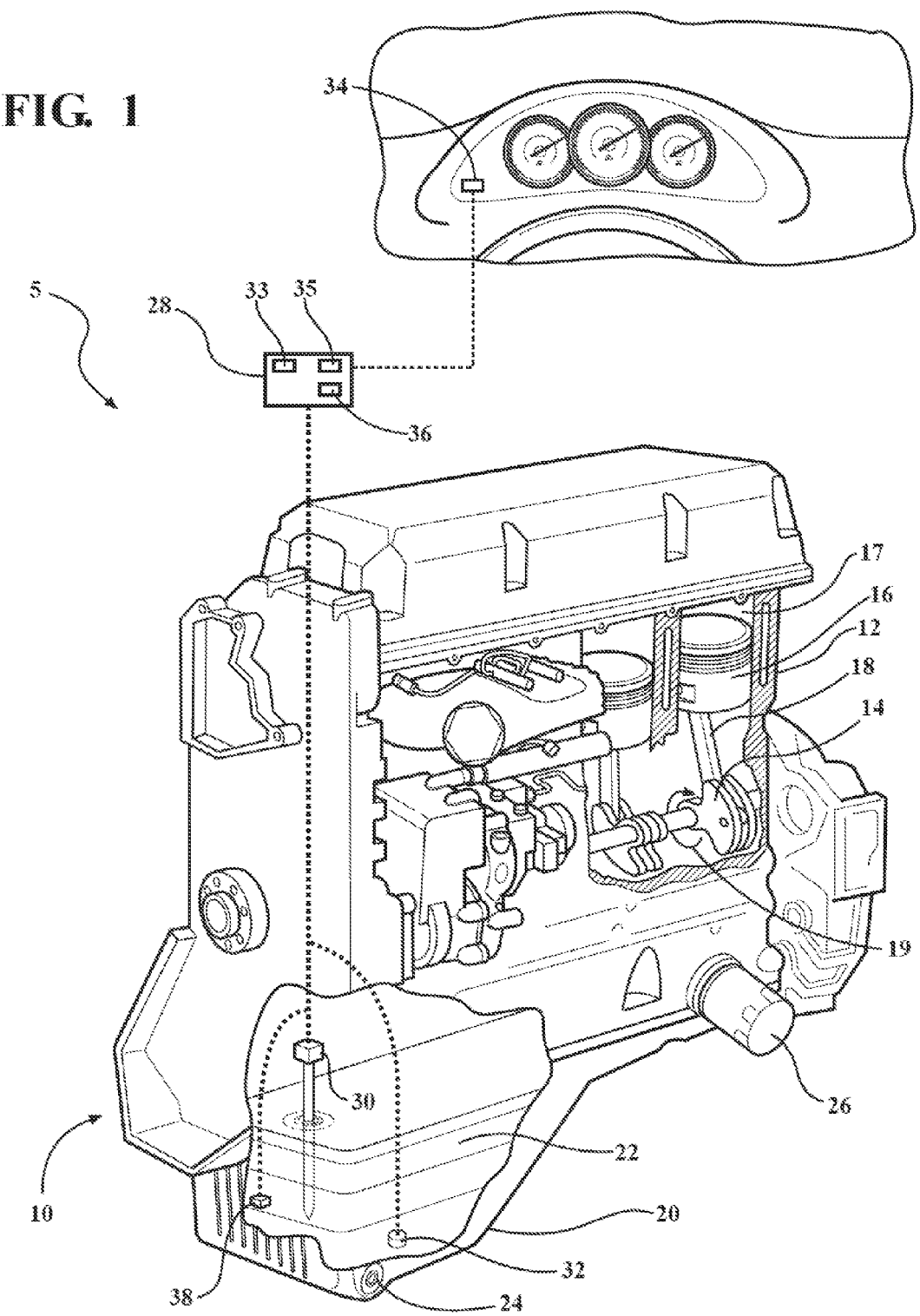
FIG. 1 is a schematic illustration of an engine oil life monitoring system.

Referring to the drawings wherein like reference numbers correspond to like or similar components throughout the several figures, FIG. 1 illustrates an automatic oil life system 5. Oil life system 5 is configured for determining remaining effective or useful life of oil utilized in an internal combustion engine prior to an oil change. The determining of the remaining oil life by oil life system 5 includes determining a number of permitted engine revolutions on a specific volume of oil.

Automatic oil life system 5 includes an internal combustion engine which is represented schematically and denoted by numeral 10. Engine 10 includes an engine block 12. Block 12 houses engine internal components such as a crankshaft 14, reciprocating pistons 16, and connecting rods 18. Pistons 16 are attached to crankshaft 14 via rods 18 to transfer the force of combustion to the crankshaft and thereby rotate the engine 10. Rotation of engine 10, which is typically measured in terms of revolutions per minute (RPM), is denoted by an arrow 19. Each connection between the respective pistons 16 and rods 18, and between the rods and crankshaft 14, includes an appropriate bearing (not shown) for smooth and reliable rotation.

Engine 10 also includes an oil pan or sump 20. Sump 20 is arranged on engine 10 and is attached to block 12 for holding a body of oil 22. Body of oil 22 is employed within engine 10 for lubricating engine's moving parts, such as bearings (not shown), pistons 16 and rods 18, and for other functions such as cooling the engine by carrying heat generated by friction and combustion away from the moving parts. Body of oil 22 additionally functions to remove contaminants from engine 10. Engine 10 additionally includes an oil filter 26 specifically configured to trap various foreign particles that the oil may collect while in service. In order to not restrict oil flow, filter 26 is generally capable of trapping particles down to only a certain size, and may thus fail to capture smaller contaminants. The body of oil 22 may also absorb soluble contaminants that are not removed by filter 26. Therefore, over time, body of oil 22 becomes chemically degraded due to oxidation and nitration, as well as contaminated with foreign materials, thus becoming less effective in its protection of engine 10, and necessitating the oil to be changed. Sump 20 includes a removable plug 24, which may be configured as a threadable fastener, for permitting body of oil 22 to be drained from the sump during an oil change.

Automatic oil life system 5 includes a controller 28, and may include a sensor 30 and a device 32, as shown. Sensor 30 is configured to sense a level or height of the body of oil 22 present in sump 20. Controller 28 may be a central processor configured to regulate operation of engine 10 or a dedicated unit programmed to solely operate the automatic oil life system. Sensor 30 is at least partially immersed in body of oil 22 and is configured to communicate such data to controller 28. Sensor 30 may be configured to sense the level of body of oil 22 either while engine 10 is shut-off, or dynamically, i.e., while the engine is running, and communicate such data to controller 28. When engine 10 is shut-off, sensor 30 may facilitate the determination of the entire volume of the oil present in the engine. On the other hand, when engine 10 is running, and a portion of the oil is in circulation throughout the engine, sensor 30 may facilitate determination of solely the volume of oil remaining in sump 20. As shown, controller 28 is also operatively connected to device 32, which may be an oil level switch configured to provide the signal when a level of oil in the sump has diminished by a predetermined amount. Device 32 is arranged in sump 20, in contact with the body of oil 22. Controller 28 receives data from each of the sensor 30 and device 32, and determines an appropriate time or instance for body of oil 22 to be changed, i.e., replaced with fresh oil.

The appropriate time or instance for changing body of oil 22 is determined according to a mathematical relationship $R(Rev)=K(Oil) \times K(Eng) \times [V_I - V_L]$, which is denoted by numeral 33. Mathematical relationship 33 is programmed and stored in the controller 28. R(Rev) represents a total number of engine revolutions permitted on a specific volume of the body of oil 22. R(Rev) may also be representative of a predetermined level of effective or useful life remaining in the body of oil 22 prior to necessitating an oil change. The factor K(Oil) represents a total number of allowed combustion events of engine 10 per liter of the body of oil 22. K(Eng) represents a number of revolutions of engine 10 for each combustion event of the engine.

$V_I$ represents an initial volume in liters of the body of oil 22 present in sump 20 after an oil change, while $V_L$ represents a volume in liters of oil lost or consumed by engine 10 from the body of oil 22. A majority of $V_L$ is typically a volume of oil that enters combustion chambers 17 during operation of engine 10, and is burned therein during the respective combustion events. Therefore, a volume in liters of the body of oil 22 that is present at any particular time in sump 20 is the result of $[V_I - V_L]$. Accordingly, the reduction in the volume of the body of oil 22 between oil changes is determined, and is thereby taken into account in calculating a respective reduction in R(Rev). Alternatively, the volume of oil consumed by engine 10 from the body of oil 22 may be based on a predetermined rate of oil consumption for a particular engine design. Such a predetermined rate of oil consumption can be established empirically during testing and evaluation of the engine.

The total number of allowed combustion events per liter of the body of oil 22, K(Oil), is an input variable in relationship 33. K(Eng) is a mathematical constant, the value of which depends on the actual engine configuration, with a specific number of cylinders. For example, in a six-cylinder, four-stroke engine, two complete engine revolutions are required for each cylinder to experience a single combustion event, i.e., K(Eng) is equal to 2 divided by 6 in the same example, and is therefore equal to a value of ⅓. $V_I$ is the initial volume in liters of the body of oil 22 determined by the rated oil capacity of engine 10, which is typically indicated at the "full" mark on an oil level indicator or dipstick (not shown), or based on the oil level in sump 20 sensed by sensor 30 after the oil change.

Subsequent to the determination of R(Rev) based on relationship 33, controller 28 executes a control action, such as activating or triggering an oil change indicator 34. Oil change indicator 34 is configured to signal to an operator of the engine or of the host vehicle when the number of engine revolutions permitted on the determined quality and volume of the body of oil 22, R(Rev), has been reached. In order to assure that the operator is reliably notified when the time for oil change has arrived, oil change indicator 34 may be positioned on an instrument panel, inside the vehicle's passenger compartment. Oil change indicator 34 may be triggered immediately upon the determination that R(Rev) has been reached, or solely after R(Rev) has been reached when the engine is started and/or shut off. Following the oil change, oil change indicator 34 is reset to represent 100% oil life remaining, and the determination of R(Rev) on a fresh body of oil may commence.

Controller 28 may additionally be programmed with a mathematical relationship $R(Rev)_{EFF}=R(Rev) \times PF_{OT}$ which is denoted by numeral 35, and with a look-up table 36. The factor $PF_{OT}$ corresponds to a penalty imposed on the number of engine revolutions permitted on the body of oil 22 due to a temperature of oil in sump 20. The factor $R(Rev)_{EFF}$ represents an effective number of engine revolutions permitted on a specific volume of oil, as adjusted or reduced for oil degradation caused by a particular elevated temperature of the body of oil in sump 20. Factors $PF_{OT}$ may be determined empirically in the course of evaluating oil for chemical degradation that results from exposure to specific temperatures during durability testing of engine 10. The look-up table 36 is then programmed to include specific factors $PF_{OT}$ that correspond to particular temperatures of the body of oil 22 in the sump 20.

To support the determination of $R(Rev)_{EFF}$, controller 28 may be configured to communicate with a sensor 38. Sensor 38 is positioned in the sump 20 and is adapted to sense temperature of the body of oil 22. In such a case, controller 28 receives the sensed oil temperature data from sensor 38, accesses the look-up table 36, and cross-references the received temperature data with the corresponding $PF_{OT}$ factor.

Accordingly, after R(Rev) is computed via mathematical relationship 33, it may be further adjusted by the mathematical relationship 35 to determine the effective number of engine revolutions permitted on a specific remaining volume of oil $R(Rev)_{EFF}$ prior to an oil change. The specific factors $PF_{OT}$ and corresponding temperatures contained in the look-up table 36 may additionally be updated via a plug-in electronic link to controller 28, or may be updated wirelessly via the internet. The described plug-in or wireless link may thereby be used by an entity authorized to service the subject vehicle, such as a vehicle dealership, to program the oil change indicator 34 to alert the vehicle operator regarding the proper time for the next oil change.

Figure 2:
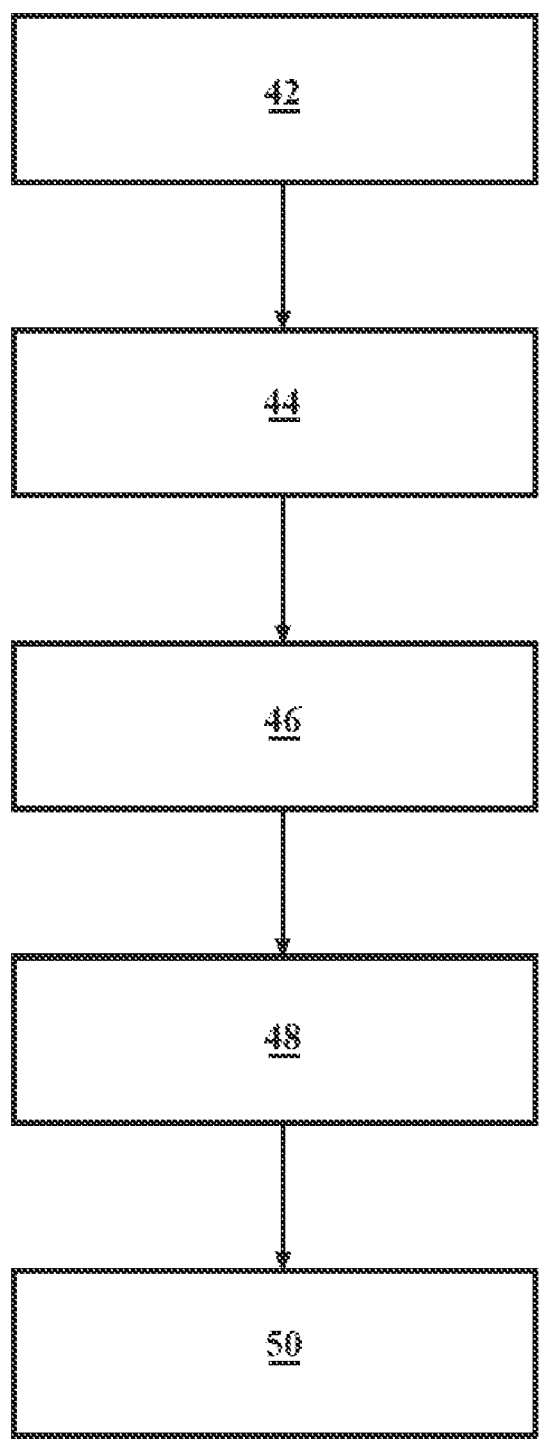
FIG. 2 is a flow chart illustrating a method for determining a number of engine revolutions permitted on a volume of oil in an internal combustion engine.

A method 40 for determining remaining oil life prior to an oil change is shown in FIG. 2, and described below with reference to the structure shown in FIG. 1. Method 40 commences in frame 42 with transferring body of oil 22 to sump 20. Following frame 42, the method proceeds to frame 44, where it includes determining volume of oil V of the transferred body of oil 22, as described above with respect to FIG. 1. After frame 44, the method advances to frame 46, where it includes determining the volume of oil consumed by the engine 10 from the transferred body of oil 22. The volume of oil consumed by engine 10 may be monitored either intermittently or continuously by device 32 and/or sensor 30 during operation of the engine, and determined via the controller 28.

Following frame 46, the method proceeds to frame 48. In frame 48, the method includes determining when the remaining oil life reaches a predetermined level. The predetermined level of remaining oil life may be established according to the number of engine revolutions R(Rev), wherein R(Rev) is based on the determined volume of the body of oil 22 and the determined volume of oil consumed by engine 10 by using the relationship 33. Additionally, as described above, after R(Rev) is determined via mathematical relationship 33, it may be further adjusted by the mathematical relationship 35 to determine the effective number of engine revolutions $R(Rev)_{EFF}$ remaining on the body of oil 22 prior to an oil change. Following frame 48, the method advances to frame 50, where it includes executing a control action, such as activating the oil change indicator 34, to signal to an operator of engine 10 or of the vehicle where the engine resides when the remaining oil life reaches the predetermined level.

While the best modes for carrying out the invention have been described in detail, those familiar with the art to which this invention relates will recognize various alternative designs and embodiments for practicing the invention within the scope of the appended claims.

The invention claimed is:

1. A method for determining remaining oil life prior to an oil change in an internal combustion engine using a body of oil, the method comprising:
   transferring the body of oil to the engine;
   determining a volume of the transferred body of oil;
   determining a volume of oil consumed by the engine from the transferred body of oil;
   determining the remaining oil life based on the determined volume of the body of oil and the determined volume of oil consumed by the engine; and
   activating an oil change indicator when the remaining oil life reaches a predetermined level.

2. The method of claim 1, further comprising resetting the oil change indicator to represent 100% of oil life remaining following the oil change.

3. The method of claim 2, wherein at least one of said determining a volume of the transferred body of oil, said determining a volume of oil consumed by the engine, said determining the remaining oil life, and said activating and said resetting the oil change indicator is accomplished via a controller operatively connected to the engine.

4. The method of claim 1, wherein the engine includes an oil sump arranged to accept the transferred body of oil, and said determining a volume of the transferred body of oil includes determining a level of the transferred body of oil in the sump.

5. The method of claim 1, wherein said determining the remaining oil life includes determining a number of revolutions for each combustion event of the engine, and further includes determining a number of combustion events permitted using the determined volume of oil.

6. The method of claim 1, wherein said determining a volume of oil consumed by the engine is accomplished via a device configured to provide a signal indicative of the volume of oil consumed by the engine.

7. The method of claim 1, wherein said determining a volume of oil consumed by the engine is accomplished based on a predetermined rate of oil consumption.

8. A system for determining remaining oil life permitted prior to an oil change in an internal combustion engine that uses a body of oil, the system comprising:
   an oil sump arranged on the engine to accept an initial body of oil;
   a sensor arranged on the engine and configured to provide a signal indicative of a volume of the initial body of oil in the sump;
   a device configured to provide a signal indicative of a volume of oil consumed by the engine; and
   a controller in communication with the sensor and the device and programmed to determine the remaining oil life based on the volume of the initial body of oil and the volume of oil consumed.

9. The system of claim 8, further comprising an oil change indicator, wherein the controller is configured to activate the oil change indicator when the remaining oil life reaches a predetermined level.

10. The system of claim 9, wherein the oil change indicator is reset to represent 100% of oil life remaining following the oil change.

11. The system of claim 8, wherein the controller is programmed with a number of revolutions for each combustion event of the engine, and the controller additionally determines the remaining oil life based on the number of revolutions for each combustion event of the engine.

12. The system of claim 8, wherein the signal indicative of a volume of the initial body of oil is indicative of a level of the initial body of oil in the sump, and the controller determines the volume based on the level.

13. The system of claim 8, wherein the controller is programmed with a number of combustion events permitted per the volume of the body of oil in the sump, and the controller additionally determines the remaining oil life based on the number of combustion events.

14. The system of claim 8, wherein the device is an oil level switch configured to provide the signal when a level of oil in the sump has diminished by a predetermined amount.

15. The system of claim 8, wherein the controller is programmed to determine the volume of oil consumed by the engine based on a rate of oil consumption, and the device is an interface port configured to communicate the rate of oil consumption to the controller.

16. A method for determining a number of engine revolutions permitted prior to an oil change in an internal combustion engine using a body of oil and having a sump, the method comprising:
   transferring the body of oil to the engine;
   determining a volume of the transferred body of oil;
   determining a volume of oil consumed by the engine from the transferred body of oil;
   determining the number of permitted engine revolutions based on the determined volume of the body of oil less the determined volume of oil consumed by the engine;
   activating an oil change indicator when the remaining oil life reaches a predetermined level; and
   resetting the oil change indicator to represent 100% of oil life remaining following the oil change.

17. The method of claim 16, wherein at least one of said determining a volume of the transferred body of oil, said determining a volume of oil consumed by the engine, said determining the number of engine revolutions, and said activating and said resetting the oil change indicator is accomplished via a controller operatively connected to the engine.

18. The method of claim 16, wherein said determining the number of engine revolutions includes determining a number of revolutions for each combustion event of the engine, and further includes determining a number of combustion events permitted using the determined volume of oil.

19. The method of claim 16, wherein said determining a volume of oil consumed by the engine is accomplished via a device configured to provide a signal indicative of the volume of oil consumed by the engine.

20. The method of claim 16, wherein said determining a volume of oil consumed by the engine is accomplished based on a predetermined rate of oil consumption.

* * * * *